United States Patent [19]
Sisley

[11] Patent Number: 5,368,550
[45] Date of Patent: Nov. 29, 1994

[54] JOINT SUPPORT

[76] Inventor: Garrett Sisley, 1295 Stonefiled St., Costa Mesa, Calif. 92626

[21] Appl. No.: 72,084

[22] Filed: Jun. 7, 1993

[51] Int. Cl.5 .............................................. A61F 5/00
[52] U.S. Cl. ........................................ 602/21; 602/63; 602/64
[58] Field of Search ............................ 602/2, 5, 6–8, 602/12, 20–23, 26, 27, 60–65; 2/16, 20, 161.1, 162

[56] References Cited

U.S. PATENT DOCUMENTS

| | | | |
|---|---|---|---|
| 4,047,250 | 9/1977 | Norman | 602/64 |
| 4,193,135 | 3/1980 | Rhee | 2/162 |
| 4,366,812 | 1/1983 | Nuzzo | 602/22 |
| 4,441,490 | 4/1984 | Nirschl | 602/21 |
| 4,716,892 | 1/1988 | Brunswick . | |
| 4,881,533 | 11/1989 | Teurlings . | |
| 4,883,073 | 11/1989 | Aziz . | |
| 4,899,763 | 2/1990 | Sebastian et al. . | |
| 4,915,097 | 4/1990 | West . | |
| 4,941,460 | 7/1990 | Working . | |
| 4,996,979 | 3/1991 | Grim et al. . | |
| 5,160,314 | 11/1992 | Peters | 602/21 |
| 5,261,871 | 11/1993 | Greenfield | 602/62 X |
| 5,267,943 | 12/1993 | Dancyger | 602/21 X |

FOREIGN PATENT DOCUMENTS 2650176  2/1991  France ................................ 602/21

Primary Examiner—Richard J. Apley
Assistant Examiner—Linda C. Dvorak
Attorney, Agent, or Firm—Walter A. Hackler

[57] ABSTRACT

A joint support includes an outer shell sized for extending across a human joint and an inner liner fixed to the outer shell for surrounding the human joint. One or more straps are provided for securing the outer shell around the human joint over the inner shell and one or more inserts, removably disposed between the outer shell and the inner liner, are provided for limiting an amount of flexion of the human joint when the strap secures the outer shell around the human joint.

14 Claims, 2 Drawing Sheets

JOINT SUPPORT

The present invention is generally directed to supports for body joints, such as wrists, elbows, knees, lower back and is more particularly directed to a support system utilizing interchangeable inserts for enabling a user to vary the amount, or degree, of flexion of the joint.

Therapeutic immobilization of joints, such as the wrist, is often necessary for preventing injury to ligaments, nerves and the bone joint itself.

Support devices have been developed to vary the degree of dorsiflexion and lateral flexion of the wrist, for example.

Some prior art wrist braces for athletes utilize a dorsal pad on the back of the hand to prevent extension. If the pads utilized are too thin, a substantial loss of support occurs, while on the other hand if the pads are too stiff, a significantly limited range of motion may occur. The present invention solves this long-standing problem by providing a support system having replaceable inserts for varying the degree of support, or limiting the amount of joint flexion.

SUMMARY OF THE INVENTION

A joint support, in accordance with the present invention, generally includes an outer shell size for extending across a human joint and an inner liner fixed to the outer shell which provides a means for surrounding the human joint.

Strap means may be provided for securing the outer shell around the human joint over the inner liner and insert means are provided for limiting the amount of flexion of the human joint when the strap means secures the outer shell around the human joint. Importantly, the insert means is removably disposed between the outer shell and the inner liner and therefore provides a means for changing the amount of flexion of the joint.

More particularly, the outer shell and the inner liner may be sized for extending across a human wrist and the inner liner may comprise a stretchable material in the form of a tube, with the joint support further comprising means for fixing the tube to the outer shell along a length of the tube.

The insert means may comprise at least one flat flexible member having means for enabling removable positioning thereof between the outer shell and the inner liner. More specifically, the means for enabling removable positioning of the flat flexible member comprises a slot therein.

Further, the flat flexible member may comprise means for distributing force applied to the flat flexible member evenly across an arm of a user. This means takes the shape of an arcuate end on the flexible member.

Another end of the flat flexible member may be formed for limiting both lateral and dorsiflexion.

Preferably the insert means comprises a plurality of flat flexible members, each having a different thickness and each having means for enabling removable positioning thereof between the outer shell and the inner liner. In this manner, the joint support provides an adjustable limitation of dorsiflexion.

BRIEF DESCRIPTION OF THE DRAWINGS

A better understanding of the present invention may be had from the consideration of the following detailed description, taken into conjunction with the accompanying drawings in which.

DETAILED DESCRIPTION

Figure 1:
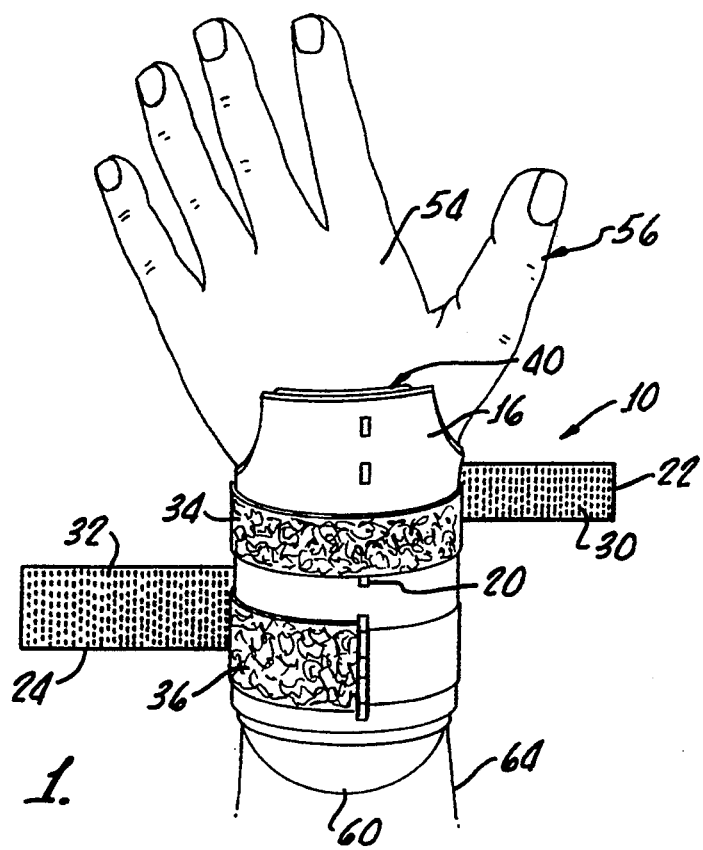
FIG. 1 is a plan view of the joint support in accordance with the present invention showing its position on top of the human wrist.
Figure 2:
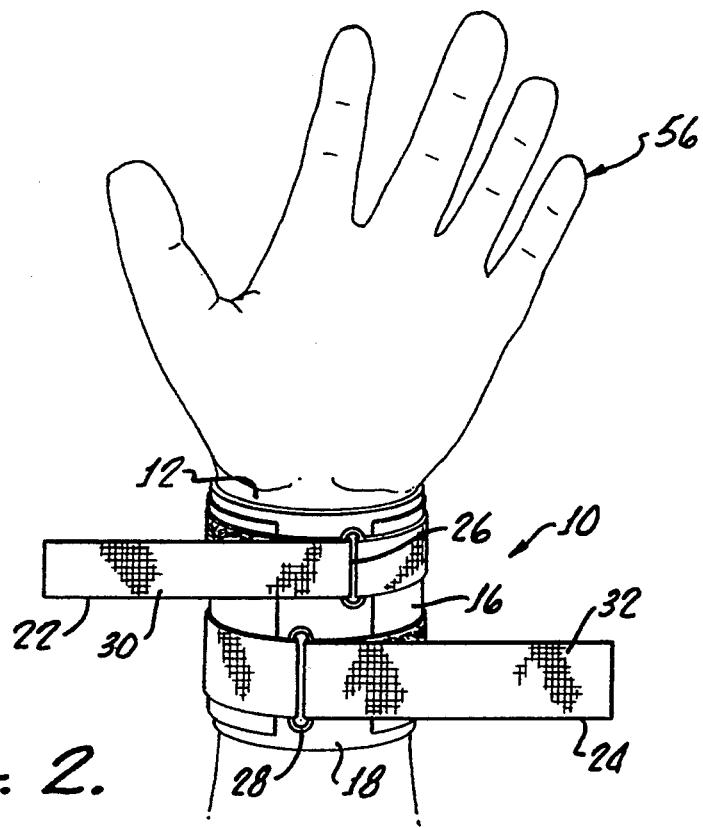
FIG. 2 is a plan view of the joint support showing its position on the bottom of a human wrist.
Figure 3:
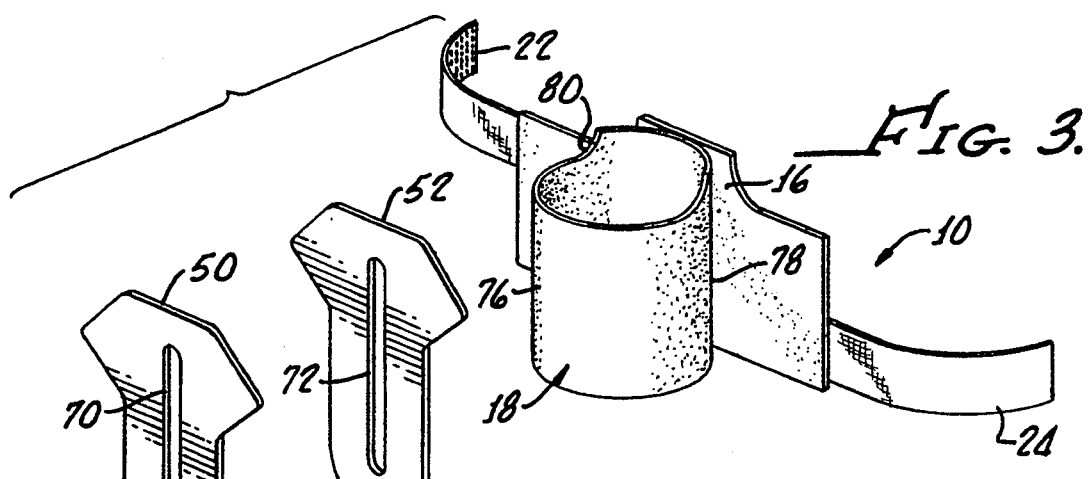
FIG. 3 is a perspective view of the joint support in accordance with the present invention showing multiple inserts before assembly.

Turning now to FIGS. 1 and 2, there is shown a joint support 10 in accordance with the present invention as it may be applied to a wrist 12 for limiting the degree of dorsal and lateral flexion of the wrist 12.

As more clearly shown in FIGS. 3–6, the joint support generally includes an outer shell 16, sized for extending across the wrist 12, and an inner liner 18 which provides a means for surrounding the wrist 12.

The outer shell 16 may be formed from a non-stretchable but flexible material, such as cordura nylon, or a canvas material. The inner liner is preferably formed from a stretchable material such as Neoprene and, taking the shape of a tube, the liner 18 is preferably sewn to the outer shell 16 along a single line 20 (see FIG. 1) extending the length of the inner liner 18 and shell 16. Straps 22, 24 sewn to the outer shell 16 provide a means for securing the outer shell around the wrist 12 over the inner liner 18 as shown in FIGS. 1 and 2.

Loops 26, 28 facilitate the installation of the joint support 10 on the wrist and the straps 22, 24 may employ a Velcro ® type of hook facing 30, 32 and pile facings 34, 36.

One or more inserts 40, 42 are provided and removably disposed between the outer shell 16 and the inner liner 18 as hereinafter described, for limiting an amount of flexion of the wrist 12 when the straps 22, 24 secure the outer shell 16 around the wrist 12.

It should be appreciated, while only two inserts 40, 42 are shown, any number of similar inserts may be utilized, with each insert being of a different thickness and/or resiliency, and formed from a material which is flexible, yet of sufficient resiliency to provide the support for the wrist 12. The inserts 40, 42 may be used singly or in combination with one another, depending upon the amount of dorsiflexion limitations desired or required by the user. The inserts 40, 42 may be formed from any suitable or flexible rubber-like Neoprene material.

The inserts 40, 42 may include a mushroom shape on one end 50, 52 thereof, which rests on back portion 54 of a user's hand 56. This mushroom shape distributes weight and pressure put on the wrist evenly across the back 54 of the hand 56 and further prevents lateral twisting and dorsiflexion of the wrist 12. Another end 60, 62 of the insert 40, 42 includes an arcuate shape which evenly distributes weight and pressure on an arm 64 of the user. Each insert 40, 42 includes a slot 70, 72 therein which is sized for slipping over the liner 18. To facilitate the installation of the inserts 40, 42 over the liner, a forward portion 76 thereof is shorter than a liner back 78 attached to the outer shell 16.

The front 76 and back 78 portions of the liner 18 are joined by an arcuate segment 80 to facilitate the sliding of the inserts 40, 42 over the liner 18 from the front portion 76 to the back portion 78.

Figure 4:
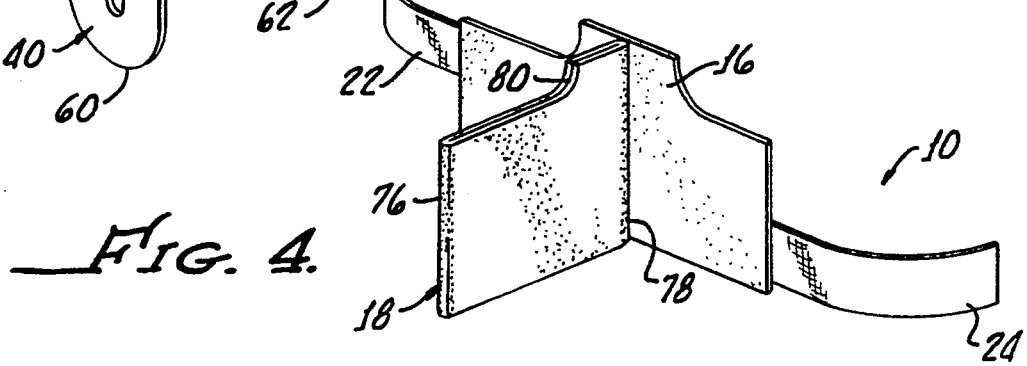
FIG. 4 is a perspective view of the present invention showing an inner liner being folded for enabling inserts to be slid therepast.
Figure 5:
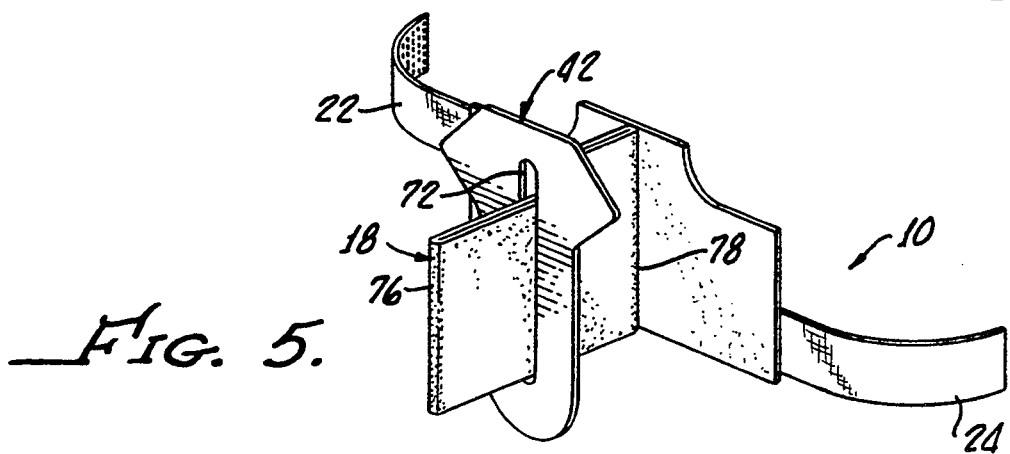
FIG. 5 is a perspective view of the present invention showing the installation of an insert over the inner liner.
Figure 6:
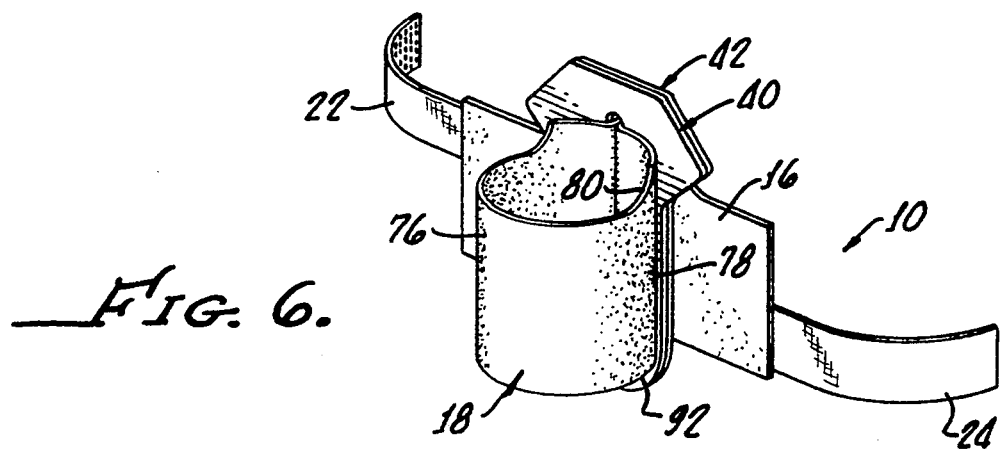
FIG. 6 is a perspective view of the present invention showing at least one insert being disposed between the inner liner and an outer shell.

The installation procedure is illustrated in FIGS. 3–6. To install one or more of the inserts 40, 42, the liner 18 is folded flat as shown in FIG. 4 and thereafter the liner 18 is pulled through the insert slot 72, as shown in FIG. 5, and thereafter the insert 42 is positioned between the liner 18 and the outer shell 16. As shown in FIG. 1, the stitching 20 does not extend to a top 90 and bottom 92 of the liner and the slot 70, 72, has a length shorter than the distance between the top 90 and bottom 92 of the liner 18 to allow the top 90 and bottom 92 to extend beyond the slot 70, 72, as shown in FIG. 6 to secure the inserts 40, 42 between the liner 18 and the outer shell 16. The natural resiliency of the liner 18 expands the liner 18 to the tubular shape, thus holding the inserts 40, 42 between the liner 18 and the outer shell 16.

The plurality of inserts 40, 42 and their removable positioning between the liner 18 and the outer shell 16 allows a user to install a less rigid insert 40 in the joint support 10, for mild support from dorsal and lateral flexion of the wrist, or installing more rigid insert 42 in the joint support 10 for greater support of the dorsal and lateral flexion of the wrist. Hence, the user may vary the degree of support of the joint support from dorsal and lateral flexion of the wrist.

Although there has been described hereinabove a specific arrangement of a joint support in accordance with the present invention, for the purposes of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the invention as defined in the appended claims.

What is claimed is:

1. A joint support comprising:
    an outer shell sized for extending across a human joint;
    inner liner means, fixed to said outer shell, for surrounding the human joint;
    strap means for securing said outer shell around said human joint over said inner liner means; and
    insert means, removably disposed between said outer shell and said inner liner means, for limiting an amount of flexion of the human joint when the strap means secures the outer shell around the human joint, said insert means comprising at least one flat flexible member having slot means for enabling removable positioning thereof between said outer shell and said inner liner means.

2. The joint support according to claim 1, wherein said inner liner means comprises a stretchable material in the form of a tube and said joint support further comprises means for fixing said tube to the outer shell along a length of said tube.

3. The joint support according to claim 1, wherein said outer shell and said inner liner means are respectively sized to extend across and surround a human wrist.

4. The joint support according to claim 3, wherein said flat flexible member comprises means, defining an arcuate end thereof, for distributing force applied to the flat flexible member evenly across an arm of a user.

5. The joint support according to claim 4, wherein said flat flexible member further comprises means, defining another end of the flat flexible member, for limiting both lateral and dorsiflexion of the wrist.

6. The joint support according to claim 1, wherein said insert means comprises a plurality of flat flexible members each having a different thickness and each having slot means for enabling removable positioning thereof between said outer shell and said inner liner means.

7. A wrist support comprising:
    an outer shell sized for extending across a human wrist;
    inner liner means, fixed to said outer shell, for surrounding the wrist;
    strap means for securing said outer shell around the wrist over said inner liner means; and
    insert means, removably disposed between said outer shell and said inner liner means for limiting an amount of dorsiflexion of the wrist when the strap means secures the outer shell around the wrist, said insert means comprising at least one flat flexible member having slot means for enabling removable positioning thereof between said outer shell and said inner liner.

8. The wrist support according to claim 7, wherein said inner liner means comprises a stretchable material in the form of a tube and said wrist support further comprise means for fixing said tube to the outer shell along a length of said tube.

9. The wrist support according to claim 7, wherein said flat flexible member comprises means, defining an arcuate end thereof, for distributing force applied to the flat flexible member evenly across the arm of a user.

10. The wrist support according to claim 9, wherein said flat flexible member further comprises means, defining another end of the flat flexible member, for limiting both lateral and dorsiflexion of the wrist.

11. The wrist support according to claim 7, wherein said insert means comprises a plurality of flat flexible members, each having a different thickness and each having slot means for enabling removable positioning thereof between said outer shell and said inner liner means.

12. A joint support comprising:
    an outer shell sized for extending across a human joint;
    inner liner means, fixed to said outer shell, for surrounding the human joint;
    strap means for securing said outer shell around said human joint over said inner liner means; and
    insert means, removably disposed between said outer shell and said inner liner means, wherein said insert means comprises a plurality of flat flexible members which overlay one another when used in combination with one another, for limiting an amount of flexion of the human joint when the strap means secures the outer shell around said human joint.

13. A wrist support comprising:
    an outer shell sized for extending across a human wrist;
    inner liner means, fixed to said outer shell, for surrounding the wrist;

strap means for securing said outer shell around the wrist over said inner liner means; and insert means, removably disposed between said outer shell and said inner liner means, for limiting an amount of dorsiflexion of the wrist when the strap means secures the outer shell around the wrist, said insert means comprising at least one flat flexible member including means, defining an arcuate shape on one end, for distributing force applied to the flat flexible member evenly across an arm of a user.

14. The wrist support according to claim 13, wherein said flat flexible member includes means, defining a mushroom shape on another end, for limiting both lateral and dorsiflexion of the wrist.

* * * * *